(12) United States Patent
Gupte

(10) Patent No.: US 12,350,335 B2
(45) Date of Patent: Jul. 8, 2025

(54) HOMEOPATHIC TOPICAL COMPOSITION

(71) Applicant: V P LYF, Thane (IN)

(72) Inventor: Vaidehi Parnad Gupte, Thane (IN)

(73) Assignee: V P LYF (IN)

( * ) Notice: Subject to any disclaimer, the term of this patent is extended or adjusted under 35 U.S.C. 154(b) by 567 days.

(21) Appl. No.: 17/777,170

(22) PCT Filed: Nov. 13, 2020

(86) PCT No.: PCT/IB2020/060686
§ 371 (c)(1),
(2) Date: May 16, 2022

(87) PCT Pub. No.: WO2021/094989
PCT Pub. Date: May 20, 2021

(65) Prior Publication Data
US 2022/0395574 A1 Dec. 15, 2022

(30) Foreign Application Priority Data
Nov. 14, 2019 (IN) .............................. 201921046308

(51) Int. Cl.
| A61K 41/00 | (2020.01) |
| A61K 9/00 | (2006.01) |
| A61K 9/12 | (2006.01) |
| A61K 33/04 | (2006.01) |
| A61K 33/06 | (2006.01) |
| A61K 33/20 | (2006.01) |
| A61K 33/42 | (2006.01) |
| A61K 36/062 | (2006.01) |
| A61K 36/185 | (2006.01) |
| A61K 36/45 | (2006.01) |
| A61K 36/87 | (2006.01) |
| A61K 36/88 | (2006.01) |
| A61K 47/10 | (2017.01) |

(52) U.S. Cl.
CPC ........ *A61K 41/0004* (2013.01); *A61K 9/0014* (2013.01); *A61K 9/12* (2013.01); *A61K 33/04* (2013.01); *A61K 33/06* (2013.01); *A61K 33/20* (2013.01); *A61K 33/42* (2013.01); *A61K 36/062* (2013.01); *A61K 36/185* (2013.01); *A61K 36/45* (2013.01); *A61K 36/87* (2013.01); *A61K 36/88* (2013.01); *A61K 47/10* (2013.01); *A61K 2236/53* (2013.01)

(58) Field of Classification Search
None
See application file for complete search history.

(56) References Cited

PUBLICATIONS

TKDL AA11/822, Dawa Bara-e-Waja-e-Niqras, Knowledge known since 1000 years TKDL AA11/822, accessed at http://www.tkdl.res.in/.
TKDL BM01/322, Pirandai, Knowledge known since 1000 years, accessed at http://www.tkdl.res.in/.
Olioso, D. et al., Effects of Gelsemium sempervirens L. on pathway-focused gene expression profiling in neuronal cells, J Ethnopharmacol. 2014.
Paarakh, P., Terminalia arjuna (Roxb.) Wt. and Arn.: A Review, International Journal of Pharmacology 6(5): 515-534, 2010.
Sticta Pulmonaria in homeopathy: properties, beneits and uses (all you need to know)—accessed at https://treasurenatural.com/sticta-pulmonaria-in-homeopathy-properties-benefits-and-uses-all-you-need-to-know/.
Kent, J., Magnesia Phosphorica from Materia Medica, accessed at https://www.materiamedica.info/en/materia-medica/james-tyler-kent/magnesia-phosphorica.

*Primary Examiner* — Michael V Meller
(74) *Attorney, Agent, or Firm* — Fox Rothschild LLP

(57) ABSTRACT

The present invention relates to a novel homeopathic composition useful for treating pain and/or inflammation comprising tinctures and/or diluted extracts. More particularly, there is provided a composition which contains a synergistic combination of extracts from *Terminalia arjuna, Sticta pulmonaria, Colchicum autumnale, Gelsemium sempervirens, Ledum palustre* and *Cissus quadrangularis*. The present invention also provides a method of preparation of the homeopathic drug composition as topical preparation, preferably as topical spray composition. *Cissus quadrangularis* extraction is also a novel process used in the composition where in cold extraction is applied for *Cissus quadrangularis*.

3 Claims, No Drawings

HOMEOPATHIC TOPICAL COMPOSITION

CROSS-REFERENCE TO RELATED APPLICATIONS

This application is a U.S. National Stage Application under 35 U.S.C. § 371 of International Application No. PCT/IB2020/060686 filed Nov. 13, 2020, which claims the benefit of Indian Patent Application number 201921046308 filed Nov. 14, 2019, the disclosures of which are hereby incorporated by reference in their entireties.

FIELD OF THE INVENTION

The present invention relates to a novel homeopathic composition useful for treating pain and/or inflammation comprising tinctures and/or diluted extracts. More particularly, there is provided a composition which contains a synergistic combination of extracts from *Terminalia arjuna, Sticta pulmonaria, Colchicum autumnale, Gelsemium sempervirens, Ledum palustre* and *Cissus quadrangularis*. The present invention also provides a method of preparation of the homeopathic drug composition for topical application as gel or cream preferably as topical spray composition.

BACKGROUND OF THE INVENTION

The history of homeopathy dates back to the eighteenth century and the research of the German physician Samuel Hahnemann, who postulated the principle of "like cures like." In the nineteenth century, Hugo Paul Friedrich Schultz postulated that toxins can have the opposite effect in small doses compared to large doses. In 1888, Schultz showed that very low concentrations of yeast toxins increased yeast growth over 100 fold. At the same time, the psychiatrist Rudolph Arndt developed his "Basic Law of Biology," which states that weak stimuli slightly accelerate the vital activity, middle-strong stimuli raise it, strong stimuli suppresses it, and very strong stimuli halt vital activity. These separate observations were formulated by Arndt in 1888 into one of the earliest laws of pharmacology representing the homeopathic effect, the Arndt-Schultz rule, which states: every stimulus on a living cell elicits an activity, which is inversely proportional to the intensity of the stimulus. This law was later restated by Ferdinand Hueppe as: for every substance, small doses stimulate, moderate doses inhibit, and large doses kill.

Allopathic medicine, with its emphasis on moderate drug doses, works to inhibit undesired physical symptoms and to kill undesired pathogens too. Homeopathic medicine, on the other hand, begins with small doses and moves towards progressively higher dilutions to stimulate the body's own natural electromagnetic forces. One of the basic tenets of homeopathic medicine is that a cure for a disease can be evoked by using a high dilution medicine that resembles, yet is different from, the cause of the disease. Further, topical Allopathic medicines for pain management may have associated side effects like skin irritation and redness.

RU02153348 disclose homeopathic drug for treatment of polyarthritis, arthrosis, rheumatism, containing *Rhus toxicodendron* and *Colchinicum autumnale* differing in that it additionally contains *Lithium carbonicum, Hepar sulfuris, Lycopodium clavatum*, and *Calcarea fluorica*.

The present invention relates to a new homeopathic composition prepared by using dilute concentrations of substances that modify the frequency of the diluent and produce a corresponding response in the human or animal body when taken externally as a topical administration, specifically a spray composition. Homeopathic compositions have been described as being effective by delivering a small amount of a substance that in large quantities would create the symptom being observed thereby allowing the body to properly develop a response that ultimately is able to eliminate the cause of the symptom being observed. A wide variety of conditions as noted are treated using the homeopathic compositions, including back ache, muscle stiffness, pain reduction, swelling, inflammation, joint pain, localized musculoskeletal injuries like sprain, strains and many others.

Currently known topical analgesic products for pain management have many problems like unpleasant physical and social side effects such as strong odors, counter irritation, redness, itching, stinging, cooling, sensitization, staining, burning and anesthesia, etc. Thus, there exists a need for the development of a new, improved topical composition that would reduce the above associated side effects with improved patient compliance.

In consideration of the need as indicated above, the inventors of the present invention have done extensive research and conducted several experiments to develop a novel topical homeopathy synergistic composition of herbal extracts with lesser associated side effects thereby rendering the composition according to the present invention as an easy-to-use composition with optimum topical effects. Further, being devoid of lesser associated side effects, instant composition has more patient compliance even if it has repeated continuous long term usage.

SUMMARY OF THE INVENTION

In one aspect the invention provides a homeopathic composition comprising;

| | |
|---|---|
| i) | *Terminalia arjuna* 2x to 8x; |
| ii) | *Sticta pulmonaria* 2x to 8x; |
| iii) | *Colchicum autumnale* 2x to 8x; |
| iv) | *Gelsemium sempervirens* 2x to 8x; |
| v) | *Ledum palustre* 2x to 8x; and |
| vi) | *Cissus quadrangularis* 2x to 8x. |

In other aspect, the invention provides a homeopathic topical composition comprising:
  (i) tinctures and/or homeopathic preparations of herbal extracts selected from the group consisting of *Terminalia arjuna, Sticta pulmonaria, Colchicum autumnale, Gelsemium sempervirens, Ledum palustre* and *Cissus quadrangularis;*
  (ii) biochemics; and
  (iii) pharmaceutically acceptable vehicle or carrier medium for topical application as spray, cream, ointment, or gel for pain and/or inflammation In another aspect, the homeopathic composition comprises:
  (i) tinctures and/or homeopathic preparations of herbal extracts selected from the group consisting of *Terminalia arjuna, Sticta pulmonaria, Colchicum autumnale, Gelsemium sempervirens, Ledum palustre* and *Cissus quadrangularis;*
  (ii) biochemics selected from *Natrum muriaticum, Natrum phosphoricum; Magnesium phosphoricum* or *Natrum sulphuricum;*
  (iii) pharmaceutically acceptable vehicle or carrier medium.

In another aspect, the present invention provides a method of preparation of the homeopathic topical composition; comprising the steps of:

a) Mixing the coarse powder of herbs (*Terminalia arjuna, Colchicum autumnale, Gelsemium sempervirens, Ledum palustre* and *Cissus quadrangularis*) with 70% dispensing alcohol and 30% purified water, setting the mixture in a glass column at room temperature and sealing the mouth of the column and setting aside for 48 hours;

b) Adding *Sticta pulmonaria* under constant stirring to solution of step a;

c) adding *Natrum muriaticum* to the solution of step b) under constant stirring;

d) adding a secondary non-aqueous solution of *Natrum phosphoricum* with stirring for 5-10 minutes to the solution of step c);

e) adding dispensing alcohol and allowing to disperse in the solution of step d);

f) filtering the dispersion as obtained in step e) to obtain a clear solution of the composition; and g) adding glycerin (optionally) to the clear solution of step f) which is sonicated and filtered to obtain the composition.

In another aspect the homeopathic composition of the present invention is filled in containers fitted with spray nozzle.

In another aspect the homeopathic composition of the present invention is dispensed in cream, ointment or gel base.

In yet another aspect the homeopathic topical composition are useful in treating pain and/or inflammation, particularly to heal muscular and bone injuries.

Another aspect of the invention is a method of treating pain by administering an effective amount of a homeopathic topical composition to a subject in need thereof.

These and other aspects and advantages of the present invention will be apparent to those skilled in the art from the following description.

DETAILED DESCRIPTION OF THE INVENTION

It should be understood that the detailed description and specific examples, while indicating embodiments of the invention, are given by way of illustration only, since various changes and modifications within the spirit and scope of the invention will become apparent to those skilled in the art. One skilled in the art, based upon the definitions herein, may utilize the present invention to its fullest extent. The following specific embodiments are to be construed as merely illustrative, and not limitative of the remainder of the disclosure in any way whatsoever.

Unless otherwise defined, all the terms used herein, including the technical and scientific terms, have the meaning as that generally understood by one of ordinary skill in the art to which the present invention relates.

Definitions

For the purpose of the disclosure, listed below are definitions of various terms used to describe the present invention. Unless otherwise indicated, these definitions apply to the terms as they are used throughout the specification and the appended claims, either individually or as part of a larger group. They should not be interpreted in the literal sense. They are not general definitions and are relevant only for this application.

It should be noted that, as used in this specification and the appended claims, the singular forms "a", "an" and "the" include plural referents unless the content clearly dictates otherwise.

It should be noted that the term "or" is generally employed in its sense including "and/or" unless the content clearly dictates otherwise.

The terms "tincture" and "homeopathic formulation" of an herb refer to extracts of a part, combinations of parts and/or the entirety of the herb as described in Homeopathic Pharmacopoeia of India. The "tincture" can be prepared by exposing a part, parts and/or the entirety of the herb in a solvent, e.g. alcohol, glycerin and/or water. The "tincture" of an herb preferably is a mother tincture of the herb prepared according to the procedures in Homeopathic Pharmacopoeia of the United States (HPUS). The "homeopathic preparation" can be prepared by dilution of the "tincture" with an appropriate liquid such as water or alcohol. The "homeopathic preparation" of an herb for the formulation of the invention is preferably prepared as per HPUS procedures, wherein the mother tincture of the herb is serially diluted and subjected to succession according to the target potency using potentization procedures known in the art of homeopathy.

The term "potency" is defined as the strength of a homeopathic remedy which is determined by how many times the remedy has been succussed and diluted during preparation. A number and a letter are associated with the remedy name to indicate which potency scale has been used. An example of the decimal scale would be *Arnica montana* 6×. An example of the centesimal scale would be *Arnica montana* 30c. An example of the 50 millesimal scale (LM) would be *Arnica montana* LM1. These are the 3 potency scales currently in use. Further, for instance, an active drug at a potency of 1× means that a tincture, preferably as defined in HPUS, of the active drug is diluted 1 in 10, e.g. 1 ml of the tincture is mixed with 9 ml of a diluent liquid, and then succussed at least 10 times, according to known potentization procedures in homeopathy. A potency of 2× means that the active drug having a potency of 1× is further diluted 1 in 10 and then succussed at least 10 times yielding the active drug at 2×.

In the present invention, herbal extracts are selected from the group consisting of but not limited to *Terminalia arjuna, Sticta pulmonaria, Colchicum autumnale, Gelsemium sempervirens, Ledum palustre* and *Cissus quadrangularis*. The extracts of these herbs at the potencies disclosed below are used as active ingredients, which are mixed and blended with other ingredients in a vehicle to form a homeopathic composition.

In an embodiment, the potency of each one of the plurality of active ingredients included in the actives portion may be one of between about tincture to about 100×, between about 1 C to about 30 C, or about LM-1 to about LM-3. The potency of each one of the plurality of active ingredients included in the actives portion may be 8×, preferably 2× to 8×.

In an embodiment, a topical spray of instant homeopathic composition may include plurality of active ingredients i.e. tinctures and/or homeopathic preparations and biochemics; and a base including a plurality of inactive ingredients. The plurality of active ingredients include tinctures and/or homeopathic preparations of *Terminalia arjuna, Sticta pulmonaria, Colchicum autumnale, Gelsemium sempervirens, Ledum palustre* and *Cissus quadrangularis*; and biochemics selected from *Natrum muriaticum, Natrum phosphoric* or *Magnesium phosphoricum, Natrum sulphuricum*, or *Calcarea sulphurica*; preferably *Natrum muriaticum* and *Natrum phosphoricum*.

In another embodiment the topical spray homeopathic formulations may include one, all, or any of the following:

The active ingredients include tinctures and/or homeopathic preparations selected from the group consisting of but not limited to herbal extracts selected from the group consisting of but not limited to *Terminalia arjuna, Sticta pulmonaria, Colchicum autumnale, Gelsemium sempervirens, Ledum palustre* and *Cissus quadrangularis*; and biochemics selected from *Natrum muriaticum, Natrum phosphoricum, Magnesium phosphoricum, Natrum sulphuricum*, or *Calcarea sulphurica*.

*Terminalia arjuna* is a well known medicinal plant used in the ancient medicine. The bark of the tree is reported to contain many bioactive compounds, which can be tapped for use in the treatment of many diseases. Vagbhata mentions arjuna in the treatment of wounds, hemorrhages and ulcers, applied topically as a powder.

*Sticta pulmonaria* is used in inflammatory rheumatism of the knee joint.

*Colchicum autumnale* (*Colchicum*) is a toxic autumn-blooming flowering plant.

*Gelsemium sempervirens* (*Gelsemium*) is a twining vine native to warm temperate and tropical America, from Guatemala north to the southeastern USA. All parts of this plant contain the toxic strychnine-related alkaloids gelsemine, gelseminine and sempervirine. At pharmacological doses, *G. sempervirens* has been reported to show sedative, analgesic and anti-seizure properties.

*Ledum palustre*: Commonly known as marsh Labrador tea, northern Labrador tea or wild rosemary, is a flowering plant in the subsection *Ledum* of the large genus *Rhododendron* in the family Ericaceae. All parts of the plant contain poisonous terpenes that affect the central nervous system. a very valuable remedy for rheumatism

*Cissus quadrangularis* a traditional medicine for joint and bone health (as well as various feminine disorders and menopause), and shows promise in promoting bone growth rates. It is popular as a joint aid for athletes, with preliminary evidence supporting this property of *cissus*.

The process of *Cissus quadrangularis* extraction used in the composition is cold extraction.

Dried *Cissus quadrangularis* is cleaned and macerated into pieces. 100 gm of *Cissus* is sonicated with alcohol and water at room temperature, post it settling down it is set in open column with Ethanol and Water if required, the column is set sealed. Post 36 hours the elute is collected and sieved. It is filtered using vacuum filtration post 24 hrs.

The inactive ingredients include menthol, alcohol, glycerin and water.

*Magnesium phosphoricum, Natrum sulphuricum, Calcarea sulphurica* are used as it brings in synergistic effect along with the herbs.

According to an embodiment the examples of topical preparations include ointment, cream, gel, spray, etc. The most preferred being application being topical spray for treating pain and/or inflammation.

The topical spray compositions of present invention may be applied onto the skin by using a sprayable dispensing device. Preferably, dispensed in a container such as a bottle or the like, fitted with a pump dispenser/nozzle or a manual metered pump that delivers a metered unit dose on actuation.

According to an embodiment the composition of the present invention contains a thickening agent or polymeric material dissolved or suspended in a liquid to yield a gel based composition.

The observed effectiveness of a given homeopathic preparation can depend upon the method used to administer it to the patient. For example, lower potency (higher concentration) homeopathic ingredients appear to have better results when used as a topical treatment application when compared to high potency ingredients. In contrast, high potency homeopathic ingredients work well when administered orally or internally.

The various components included in implementations of homeopathic preparations disclosed here are selected from those officially listed in the Homeopathic Pharmacopoeia of the United States (HPUS) and Homeopathic Pharmacopoeia of India. Table 1 is a listing of all active ingredients (components) that may be used in the various preparations of the instant invention along with the range of dilutions that may be utilized for each. In this table, tincture refers to the mother tincture as defined in the HPUS.

TABLE 1

| Active Ingredient | |
|---|---|
| Component | Dilution Range |
| *Terminalia arjuna* | Tinct. - 100x, 1C-30C, LM-1 to LM-3 |
| *Sticta pulmonaria* | Tinct. - 100x, 1C-30C, LM-1 to LM-3 |
| *Colchicum autumnale* | Tinct. - 100x, 1C-30C, LM-1 to LM-3 |
| *Gelsemium sempervirens* | Tinct. - 100x, 1C-30C, LM-1 to LM-3 |
| *Ledum palustre* | Tinct. - 100x, 1C-30C, LM-1 to LM-3 |
| *Cissus quadrangularis* | Tinct. - 100x, 1C-30C, LM-1 to LM-3 |

A wide variety of combinations of potential active ingredients at desired potencies are possible using the ingredients and dilutions listed in Table 1. In the instant invention, various implementations of a topical spray preparation, and/or bottle containing a dispensing dropper preparation and/or in a roll-on bottle and/or in any form of creams or ointments or serums or oils or emulsifications are disclosed. Those of ordinary skill in the art will readily be able to create additional implementations using the principles disclosed herein.

According to an embodiment of the present invention there is provided a homeopathic composition comprising

| i) | *Terminalia arjuna* 2x to 8x; |
|---|---|
| ii) | *Sticta pulmonaria* 2x to 8x; |
| iii) | *Colchicum autumnale* 2x to 8x; |
| iv) | *Gelsemium sempervirens* 2x to 8 x; |
| v) | *Ledum palustre* 2x to 8x; and |
| vi) | *Cissus quadrangularis* 2 x to 8 x. |

According to an embodiment of the present invention the composition may comprise biochemics and pharmaceutically acceptable vehicle or carrier.

The composition of the present invention is an effective formulation that does not have toxicity and tackles pain and inflammation effectively.

TABLE 2

Actives Composition

| Name | Drug Strength | Physical form | Strong Alcohol (in ml) | Mother Tincture made (in ml) |
|---|---|---|---|---|
| Terminalia arjuna | 1/10 | Coarse powder | 100 g 400 | 635 1000 |
| Colchicum autumnale | 1/10 | Coarse powder | 100 g 200 | 824 1000 |
| Ledum palustre | 1/10 | Coarse powder | 100 g 500 | 537 1000 |
| Cissus quadrangularis | 1/10 | Coarse powder | 100 g 400 | 635 1000 |

TABLE 3

Actives Implementation

| Name | Potency | Tincture (in parts) | Purified water (in parts) | Strong alcohol (in parts) |
|---|---|---|---|---|
| Terminalia arjuna | 2x | 1 | 3 | 6 |
| Sticta pulmonaria | 2x | 1 | 3 | 6 |
| Colchicum autumnale | 2x | 1 | 3 | 6 |
| Gelsemium sempervirens | 2x | 1 | 4 | 5 |
| Ledum palustre | 2x | 1 | 3 | 6 |
| Cissus quadrangularis | 2x | 1 | 3 | 6 |

TABLE 4

Actives preparation as per Monograph from HPI Vol1 (Part1)

| Serial No. | Active Ingredients (HPUS) | Dilution | % of Weight of Actives |
|---|---|---|---|
| 1. | Terminalia arjuna | 8× | 3.632% |
| 2. | Sticta pulmonaria | 8× | Not less than 0.85 percent w/v. |
| 3. | Colchicum autumnale | 8× | 3.632% |
| 4. | Gelsemium sempervirens | 0.850 g to 0.910 g of water 76.0 to 80.0 percent v/v. of alcohol | Not less than 1.50 percent w/v |
| 5. | Ledum palustre | 8× | 3.632% |
| 6. | Cissus quadrangularis | 100 gm in 700 ml of Dispensing alcohol and 350 ml of purified water. From the elute 200 ml was used for the spray | |

TABLE 5

Base Implementation

| Serial No. | Inactive Ingredients | % of Weight of inactive |
|---|---|---|
| 1. | Purified water | 30% |
| 2. | Menthol | Upto 20% |
| 3. | Glycerin | Upto 10% |
| 4. | Dispensing Alcohol | Upto 70% |

Process for the Preparation of Composition of the Present Invention:

In an aspect, the present invention
i) all the herbs namely *Terminalia arjuna, Sticta pulmonaria, Colchicum autumnale, Gelsemium sempervirenaria, Ledum palustere* and *Cissus quadrangularis* are measured to 50 gm individually. Columns are setup and each herb is set in the column with purified water and alcohol in ratio of 30:70. The columns are sealed pack and kept for 48 hours.
ii) Biochemics like *Natrum muriaticum, Natrum phosphoricum, Magnesium phosphoricum, Natrum sulphuricum, Calcarea sulphurica* are added to the column of *Cissus quadrangularis*.
iii) Elute is filtered. All elutes are then mixed in equal proportions. All elutes are then mixed in equal proportions. Purified water is added to the mixture of elutes. It is again filtered. Menthol is added by dissolving it in alcohol. Glycerin is added and entire solution is sonicated In an aspect, the present invention relates to a process for the preparation of a homeopathic topical composition comprising the steps of:
a) Mixing the coarse powder of herbs (*Terminalia arjuna, Colchicum autumnale, Gelsemium sempervirens, Ledum palustre* and *Cissus quadrangularis*) with 70% dispensing alcohol and 30% purified water, setting the mixture in a glass column at room temperature and sealing the mouth of the column and setting aside for 48 hours;
b) adding *Sticta pulmonaria* under constant stirring to solution of step a)
c) adding *Natrum muriaticum* to the solution of step b) under constant stirring;
d) adding a secondary non-aqueous solution of *Natrum phosphoricum* with stirring for 5-10 minutes to the solution of step c);
e) adding dispensing alcohol and allowing to disperse in the solution of step d);
f) filtering the dispersion as obtained in step e) to obtain a clear solution of the composition.

In another embodiment of the present invention glycerin is added to the clear solution of step f) which is sonicated and filtered to obtain the composition.

It will be evident to one skilled in the art that the present invention is not limited to the above description or illustrative examples provided below, and that it can be embodied in other specific forms without departing from the essential attributes thereof. It is therefore desired that the description and examples be considered in all respects as illustrative and not restrictive, reference being made to the appended claims, and all changes which come within the meaning and range of equivalency of the claims are therefore intended to be embraced therein. Accordingly, the following examples are intended to illustrate but not to limit the scope of the present invention.

EXAMPLES IN ACCORDANCE WITH THE PRESENT INVENTION

Example 1

The Topical Composition of Homeopathy Composition

Batch 1

| Ingredients | |
|---|---|
| Terminalia Arjuna | 100 ml/1000 ml |
| Ledum palustre | 100 ml/1000 ml |
| Cissus quadrangularis | 200 ml/1000 ml |
| Sticta pulmonaria | 100 ml/1000 ml |

Batch 1

| Ingredients | |
|---|---|
| *Gelsemium sempervirens* | 100 ml/1000 ml |
| *Colchicum autumnale* | 100 ml/1000 ml |
| Menthol | 10 g/1000 ml |
| Dispensing alcohol | 700 ml |
| Purified Water | 300 ml |

Procedure:
a. 200 ml of *Cissus quadrangularis* extract made in House and 100 ml of *Ledum palustre* added in a beaker,
b. Half of 50 ml each of {*Magnesium phosphoricum*+*Natrum sulphuricum*+*Calcarea sulphurica*} was added to it (liquids),
c. Dispensing Alcohol (70%)+Purified Water (30%) was added,
d. The resulting solution was allowed to attain a temperature of 20-25° C.
e. The dispersion as obtained in step (d) was homogenized for 15 minutes at 4200 rpm and stirred for 120 minutes and filtered one or more times through PES filter to obtain a clear solution, Filtered twice to get clear solution
f. 100 ml of extract made In House of *Terminalia arjuna* was added to the above solution
g. 100 ml of mother tincture of *Sticta pulmonaria* and *gelsemium* was added to the above solution
h. 100 ml of extract made In House of *Colchicum* were added to the solution
i. The resulting solution was allowed to attain a temperature of 20-25° C.
j. The dispersion as obtained in step (i) was sonicated for 15 minutes stirred for 120 minutes and filtered one or more times through PES filter to obtain a clear solution,
k. Other half of 50 ml each of {*Magnesium phosphoricum*+*Natrum sulphuricum*+*Calcarea sulphurica*} added to it (liquids)
l. The resulting solution was allowed to attain a temperature of 20-25° C.
m. The dispersion as obtained in step (1) was sonicated for 15 minutes stirred for 120 minutes and filtered one or more times through PES filter to obtain a clear solution, Elute:

| | |
|---|---|
| *Cissus quadrangularis* | 200 ml Q |
| *Ledum palustre* | 100 ml Q |
| *Terminalia arjuna* | 100 ml Q |
| *Sticta pulmonaria* | 100 ml Q |
| *Gelsemium* | 100 ml Q |
| *Colchicum* | 100 ml Q |
| 10 mg of Menthol dissolved in 100 ml of Purified Water | |

Example 2

The Topical Composition of Homeopathy Composition

Batch 2

| Ingredients | |
|---|---|
| *Terminalia Arjuna* | 100 ml/1000 ml |
| *Ledum palustre* | 100 ml/1000 ml |
| *Cissus quadrangularis* | 200 ml/1000 ml |
| *Sticta pulmonaria* | 100 ml/1000 ml |
| *Gelsemium sempervirens* | 100 ml/1000 ml |
| *Colchicum autumnale* | 100 ml/1000 ml |
| Menthol | 20 g/1000 ml |
| Dispensing alcohol | 700 ml |
| Purified Water | 300 ml |

Procedure:
a. 200 ml of *Cissus quadrangularis* extract made in House and 100 ml of *Ledum palustre* extract made In House was added in a beaker
b. Half of 50 ml each of {*Magnesium phosphoricum*+*Natrum sulphuricum*+*Calcarea sulphurica*} was added to it (liquids),
c. Dispensing Alcohol (70%)+Purified Water (30%) was added,
d. The resulting solution was allowed to attain a temperature of 20-25° C.
e. The dispersion as obtained in step (d) was homogenized for 15 minutes at 4200 rpm and stirred for 120 minutes and filtered one or more times through PES filter to obtain a clear solution, Filtered twice to get clear solution
f. 100 ml of extract made In House of *Terminalia arjuna* was added to the above solution
g. 100 ml of mother tincture of *Sticta pulmonaria* and *Gelsemium* was added to the above solution
h. 100 ml of extract made In House of *Colchicum* were added to the solution
i. The resulting solution was allowed to attain a temperature of 20-25° C. The dispersion as obtained in step (e) was sonicated for 15 minutes stirred for 120 minutes and filtered one or more times through PES filter to obtain a clear solution,
j. Other Half of 50 ml each of {*Magnesium phosphoricum*+*Natrum sulphuricum*+*Calcarea sulphurica*} added to it (liquids)
k. The resulting solution was allowed to attain a temperature of 20-25° C.
l. The dispersion as obtained in step (j) was sonicated for 15 minutes stirred for 120 minutes and filtered one or more times through PES filter to obtain a clear solution, Elute:

| | |
|---|---|
| *Cissus quadrangularis* | 200 ml Q |
| *Ledum palustre* | 100 ml Q |
| *Terminalia arjuna* | 100 ml Q |
| *Sticta pulmonaria* | 100 ml Q |
| *Gelsemium* | 100 ml Q |
| *Colchicum* | 100 ml Q |
| 20 mg of Menthol dissolved in 100 ml of Purified Water | |

Example 3

The Topical Composition of Homeopathy Composition

Batch 3

| Ingredients | mL/mL per ml |
| --- | --- |
| *Terminalia Arjuna* | 100 ml/1000 ml |
| *Ledum palustre* | 100 ml/1000 ml |
| *Cissus quadrangularis* | 200 ml/1000 ml |
| *Sticta pulmonaria* | 100 ml/1000 ml |
| *Gelsemium* | 100 ml/1000 ml |
| *Colchicum* | 100 ml/1000 ml |
| Menthol | 20 g/1000 ml |
| Glycerin | 50 ml/1000 ml |
| Dispensing alcohol | 700 ml |
| Purified Water | 300 ml |

Procedure:

a. 200 ml of *Cissus quadrangularis* extract made In House was and 100 ml of *Ledum palustre* extract made In House added in a beaker b. Half of 50 ml each of {*Magnesium phosphoricum+Natrum sulphuricum+Calcarea sulphurica*} was added to it (liquids), c. Dispensing Alcohol (70%)+Purified Water (30%) was added, d. The resulting solution was allowed to attain a temperature of 20-25° C. The dispersion as obtained in step (e) was homogenized for 15 minutes at 4200 rpm and stirred for 120 minutes and filtered one or more times through PES filter to obtain a clear solution, Filtered twice to get clear solution e. 100 ml of mother tincture of *Terminalia arjuna* was added to the above solution f. 100 ml of mother tincture of *Sticta pulmonaria* was added to the above solution g. 100 ml of mother tincture of each *Gelsemium* and *Colchicum* were added to the solution h. The resulting solution was allowed to attain a temperature of 20-25° C. The dispersion as obtained in step (g) was sonicated for 15 minutes stirred for 120 minutes and filtered one or more times through PES filter to obtain a clear solution, i. Other half of 50 ml each of {*Magnesium phosphoricum+Natrum sulphuricum+Calcarea sulphurica*} added to it (liquids)

j. Glycerin was added to the solution to increase the viscosity.

k. The resulting solution was allowed to attain a temperature of 20-25° C.

l. The dispersion as obtained in step (k) was sonicated for 15 minutes stirred for 120 minutes and filtered one or more times through PES filter to obtain a clear solution.

Elute:

| | |
| --- | --- |
| *Cissus quadrangularis* | 200 ml Q |
| *Ledum palustre* | 100 ml Q |
| *Terminalia arjuna* | 100 ml Q |
| *Sticta pulmonaria* | 100 ml Q |
| *Gelsemium* | 100 ml Q |
| *Colchicum* | 100 ml Q |
| 20 mg of Menthol dissolved in 100 ml of Purified Water | |
| 10 ml of Glycerin | |

The clear solution obtained above is filled in spray bottles. The composition of the present invention is applied topically by means of a spray.

In embodiment the clear solution obtained above is mixed with gel base for topical administration.

In embodiment the clear solution obtained above is mixed with cream base for topical administration.

Evaluation of Anti-Inflammatory and Analgesic Activity of Topical Formulations:

VP3 Formulation (Comparative):

*Cissus quadrangularis*
*Terminalia Arjuna*
*Ledum palustre*
*Gelsemium sempervirens*
*Natrum muriaticum*

VP2 Formulation According to the Present Invention:

*Cissus quadrangularis*
*Terminalia Arjuna*
*Ledum palustre*
*Gelsemium sempervirens*
*Sticta pulmonaria*
*Colchicum autumnale*
*Natrum muriaticum*

Experiment 1

Anti-Inflammatory Activity of Formulations on Carrageenan-Induced Paw Edema in Rats Anti-inflammatory activity of different formulations was evaluated in carrageenan-induced paw edema in male Sprague-Dawley rats weighing about 225 g. Thirty minutes before carrageenan injection, the formulations VP2, VP3 were applied on the left hind paw of the rats at the dose of 0.35 ml.

Control group received vehicle only.

Each group had 6 animals.

Then, 0.1 ml of 1% carrageenan in physiological saline was injected into the paw subplantarly. Immediately, 1, 2, 3 and 4 hours after the carrageenan injection, the thickness of the paw was measured using a digital vernier caliper, and the percent swelling of the paw and the percent inhibition of the edema formation were calculated as follows:

% swelling at a timepoint=[(paw thickness−initial paw thickness)/initial paw thickness]×100%
inhibition=[1−(% swelling of drug-treated group/% swelling of control group)]×100

The results are represented in table 6

TABLE 6

Effect of formulations on carrageenan-induced paw edema

| Group | 1 hrs | | 2 hrs | | 3 hrs | | 4 hrs | |
|---|---|---|---|---|---|---|---|---|
| | % Swelling | % Inhibition | % Swelling | % Inhibition | % Swelling | % Inhibition | % Swelling | % Inhibition |
| Control | 70.03 ± 16.09 | — | 97.25 ± 10.09 | — | 101.78 ± 16.33 | — | 121.22 ± 28.08 | — |
| VP2 | 38.64 ± 12.54* | 44.82 | 52.02 ± 17.95* | 46.50 | 56.07 ± 17.60* | 44.90 | 56.59 ± 20.38* | 53.31 |
| VP3 | 37.81 ± 18.17* | 46.01 | 57.88 ± 28.35* | 40.48 | 61.97 ± 24.27* | 39.11 | 65.46 ± 27.04 | 45.99 |

*$p < 0.05$ vs. control group (One-way ANOVA, followed by Dunnett's post hoc test)

As can be seen in Table 6, the formulations according to the present invention exhibited significant decrease of % swelling of the paw compared to the control. The % inhibition of the edema formation by the formulations was maximum with VP2, which is in range of 44.82% to 53.31.

In formulation without *Sticta* and *Colchicum*, there was significant drop in the activity noted.

Experiment 2

Analgesic Activity of Formulations on Carrageenan-Induced Paw Edema in Rats

Analgesic activity was evaluated against hypernociception induced in the hindpaw by the administration of an intraplantar carrageenan suspension and was measured according to the paw pressure tests of Randall Selitto. In the Randall Selitto test, an analgesy-meter with a cone-shaped paw-presser with a rounded tip, which applies a linearly increasing force to the plantar surface of the paw, was used. The weight in grams (g) required to elicit nociceptive responses such as paw flexion or struggling was defined as the nociceptive threshold. The mechanical evaluation of hypernociception intensity was evaluated 3 hrs after the carrageenan injection.

The results are represented in table 7.

TABLE 7

The mechanical evaluation of formulations against hypernociception intensity (Δ withdrawal threshold in grams)

| Group | Δ withdrawal threshold (g) |
|---|---|
| Control | 84.25 ± 7.35 |
| VP2 | 128.14 ± 10.78* |
| VP3 | 122.82 ± 7.15* |

*$p < 0.05$ vs. control group (One-way ANOVA, followed by Dunnett's post hoc test)

As can be seen in Table 7, the formulations according to the present invention exhibited significant attenuation of Δ withdrawal threshold compared to the control group.

Maximum attenuation was observed with the formulation VP2.

Experiment 2

Skin Irritation Study in Rabbits

The acute dermal irritation study was performed in accordance with the OECD Guidelines 404 for "Acute dermal irritation/corrosion" on male White New Zealand rabbits (2.5-3 kg). Briefly, approximately 24 hours before the test, around 5 cm×5 cm of rabbit's dorsal area of the trunk was clipped for experimental use. 0.5 ml formulation was then applied under a 2.5 cm×2.5 cm gauze patch and wrapped with occlusive dressing. The test sites were observed and scored for erythema and oedema at 1 h, 24 h, 48 and 72 h post-exposure with formulation. Dermal responses were determined in accordance with OECD guidelines. Erythema and oedema were scored on a scale of 0-4, with 0 showing no effect and 4 representing severe symptoms. Since formulation was expected to be safe, limit test was performed in one rabbit as per OECD guideline 404.

TABLE 8

| Group | Observation |
|---|---|
| VP2 | No sign of irritations till 72 hrs post-exposure |

As can be seen in Table 8, formulation did not show any signs of irritations till 72 hrs post-exposure.

Thus the topical formulation of the present invention is safe.

Although shown and described in what is believed to be the most practical and preferred embodiments, departures from the specific formulation and process described may be apparent to those skilled in the art and may be used without departing from the scope of the present invention.

The invention claimed is:

1. A process for preparing a homeopathic composition consisting essentially of:
   a) mixing *Terminalia arjuna*, *Colchicum autumnale*, *Gelsemium sempervirens*, *Ledum palustre* and *Cissus quadrangularis* with 70% of alcohol and 30% purified water;
   b) setting the mixture in a glass column at room temperature and sealing the mouth of the column and setting aside for 48 hours;
   c) adding *Sticta pulmonaria* under constant stirring to the mixture in b) to create a solution;
   d) adding alcohol to the solution of c) and allowing it to disperse; and
   e) filtering the dispersion in d) to obtain a clear solution of the homeopathic composition.

2. The process for preparing the homeopathic composition of claim 1, wherein glycerin is added to the clear solution of (e) which is sonicated and filtered to obtain the homeopathic composition.

3. The process for preparing the homeopathic composition of claim 1, wherein the homeopathic composition is mixed with a gel base or a cream base to yield a topical gel formulation or a topical cream formulation.

* * * * *